(12) United States Patent
Teramura et al.

(10) Patent No.: US 9,914,695 B2
(45) Date of Patent: *Mar. 13, 2018

(54) TWO-STEP PROCESS FOR PREPARING 3-SUBSTITUTED PHENYLALKYLAMINES

(71) Applicant: Mallinckrodt LLC, Hazelwood, MO (US)

(72) Inventors: Doug Teramura, Hazelwood, MO (US); Subo Liao, Hazelwood, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/202,670

(22) Filed: Jul. 6, 2016

(65) Prior Publication Data

US 2017/0008832 A1    Jan. 12, 2017

Related U.S. Application Data

(60) Provisional application No. 62/190,975, filed on Jul. 10, 2015.

(51) Int. Cl.
*C07C 213/02* (2006.01)
*C07C 45/69* (2006.01)

(52) U.S. Cl.
CPC .......... *C07C 213/02* (2013.01); *C07C 45/69* (2013.01); *C07B 2200/07* (2013.01)

(58) Field of Classification Search
None
See application file for complete search history.

(56) References Cited

U.S. PATENT DOCUMENTS

| | | |
|---|---|---|
| 4,113,781 A | 9/1978 | Aquila |
| 6,248,737 B1 | 6/2001 | Buschmann |
| 6,344,558 B1 | 2/2002 | Buschmann |
| RE39,593 E | 4/2007 | Buschmann |
| 7,417,170 B2 | 8/2008 | Hell |
| 8,138,376 B2 | 3/2012 | Filliers |
| 8,552,219 B2 | 10/2013 | Bhirud |
| 8,669,399 B2 | 3/2014 | Buschmann |
| 8,704,002 B2 | 4/2014 | Jagusch |
| 9,556,108 B2 | 1/2017 | Liao |
| 2006/0167318 A1 | 7/2006 | Jagusch |
| 2006/0194988 A1 | 8/2006 | Hell |
| 2009/0326271 A1 | 12/2009 | Hell |
| 2011/0306793 A1 | 12/2011 | Buschmann |
| 2013/0060065 A1 | 3/2013 | Jagusch |
| 2013/0137890 A1 | 5/2013 | Rajadhyaksha |
| 2013/0150622 A1 | 6/2013 | Fandrick |
| 2013/0338399 A1 | 12/2013 | Buschmann |
| 2016/0009635 A1 | 1/2016 | Liao |

FOREIGN PATENT DOCUMENTS

| | | |
|---|---|---|
| CA | 2285578 A1 | 7/1999 |
| EP | 2545028 | 7/2013 |
| WO | 2008/012046 A1 | 1/2008 |
| WO | 2008012283 A1 | 1/2008 |
| WO | 2011/026314 A1 | 3/2011 |
| WO | 2011080736 A1 | 7/2011 |
| WO | 2011/107876 A2 | 9/2011 |
| WO | 2013090161 A1 | 6/2013 |

OTHER PUBLICATIONS

International Search Report and Written Opinion from related international application No. PCT/US16/41027 dated Sep. 26, 2016, 9 pages.
Ma, A Palladium/Chiral Amine Co-catalyzed Enantioselective Dynamic Cascade Reaction: Synthesis of Polysubstituted Carbocycles with a Quaternary Carbon Stereocenter, Angewandte Chemie International Edition, 2013, pp. 6050-6054, vol. 52(23).
Ibrahem, Palladium/Chiral Amine Co-catalyzed Enantioselective B-Arylation of a,B-Unsaturated Aldehydes, 2013, pp. 878-882, vol. 52.
Hayashi, Asymmetric 1,4-Addition of Arylboronic Acids to a,B-Unsaturated Aldehydes Catalyzed by a Chiral Diene-Rhodium Complex, Chemistry Letters, Sep. 28, 2005, pp. 1480-1481, vol. 34(11).
Chun-Hui, Rh(I)/diene-catalyzed addition reactions of aryl/alkenylboronic acids with aldehydes, Tetrahedron Letters, 2009, pp. 4953-4957, vol. 50(35).
Qiang, A practical and enantioselective synthesis of tapentadol, Tetrahedron: Asymmetry, 2012, pp. 577-582, vol. 23.

*Primary Examiner* — Clinton Brooks

(57) ABSTRACT

Processes for preparing 3-substituted phenylalkylamines comprising reacting a phenyl boronic compound with an α-β unsaturated carbonyl-containing compound via an asymmetric 1,4-addition reaction, followed by reductive alkylation. The processes may be useful in the synthesis of tapentadol.

20 Claims, No Drawings

TWO-STEP PROCESS FOR PREPARING 3-SUBSTITUTED PHENYLALKYLAMINES

CROSS-REFERENCE TO RELATED APPLICATIONS

This application claims the priority of U.S. Provisional Application Ser. No. 62/190,975, filed Jul. 10, 2015, the disclosure of which is hereby incorporated by reference in its entirety.

FIELD

The present disclosure generally relates to the synthesis of 3-substituted phenylalkylamines via a catalytic asymmetric 1,4-addition reaction.

BACKGROUND

Tapentadol (i.e., 3-[(1R, 2R)-3-(dimethyamino)-1-ethyl-2-methylpropyl] phenol) is a small organic molecule that is used as an analgesic. Tapentadol is known to have a dual mechanism of action as an agonist of the μ-opioid receptor and also as a norepinephrine (NE) reuptake inhibitor (NRI) for improved analgesic efficacy especially in chronic or neuropathic pain disorders.

Several different routes for preparing tapentadol have been reported. A typical method is to produce a racemic mixture of intermediates that must be separated by chiral chromatographic separation or by chiral resolution. The separation of chiral compounds, however, can be technically challenging, time consuming, or both.

There are a few asymmetric syntheses for the preparation of tapentadol that do not require chiral separation or chiral resolution, but rather relies on a direct asymmetric synthesis of chiral compounds. These syntheses can be moderately efficient. Yet, these syntheses consist of multiple reaction steps and have protection/deprotection steps of functional groups within the synthesis. Developing a more expedite synthetic process where no protecting groups are utilized or where a synthetic step is coupled with a deprotection step would provide a shorter synthesis, reduced cost, and a time savings.

SUMMARY

Provided herein are processes for preparing chiral 3-substituted phenylalkylamines via catalytic asymmetric 1,4-addition reactions.

One aspect of the present encompasses a process for preparing a compound of Formula (III). The process comprises contacting a compound of Formula (I) with a compound of Formula (IV) in the presence of a transition metal catalyst and a chiral ligand to form a compound of Formula (II). The process further comprises contacting the compound of Formula (II) with a secondary amine having Formula (V) to form the compound of Formula (III). The process for preparing the compound of Formula (III) is illustrated as follows:

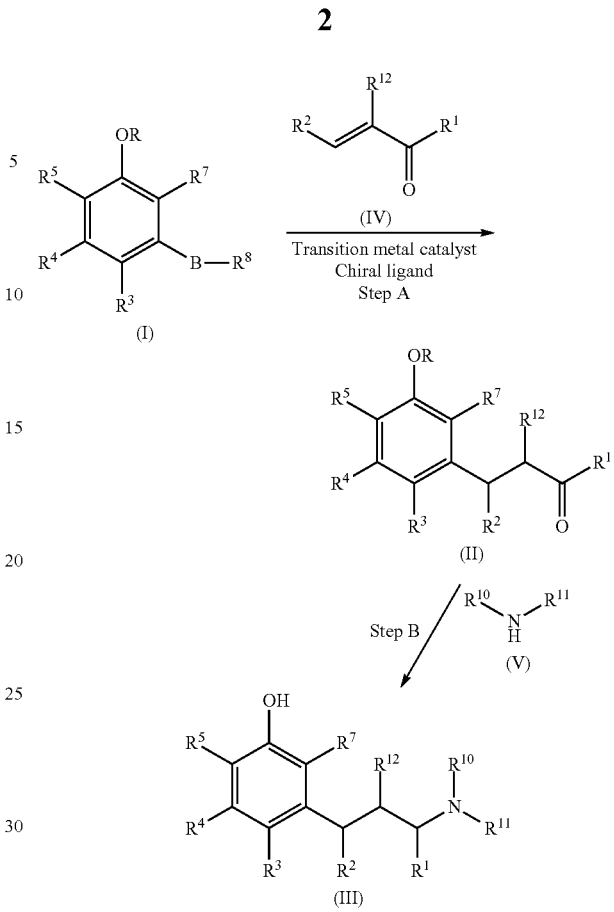

wherein:
R is hydrogen, alkenyl, substituted alkenyl, aryl, or substituted aryl;
$R^1$ is hydrogen, $OR^{20}$, $NR^{20}R^{21}$, $SR^{20}R^{21}$, hydrocarbyl, or substituted hydrocarbyl;
$R^2$ is hydrocarbyl or substituted hydrocarbyl;
$R^3$, $R^4$, $R^5$, and $R^7$ are independently hydrogen, $OR^{20}$, $NR^{20}R^{21}$, $SR^{20}R^{21}$, halo, hydrocarbyl, or substituted hydrocarbyl;
$R^8$ is

—O—$(CR^{13}R^{14})_n$—O—, or trihalo;
$R^{10}$ and $R^{11}$ are independently hydrocarbyl, substituted hydrocarbyl, or $R^{10}$ and $R^{11}$ together may form a ring or ring system selected from carbocyclic, heterocyclic, aryl, heteroaryl, or combinations thereof;
$R^{12}$ is hydrocarbyl or substituted hydrocarbyl;
$R^{13}$ and $R^{14}$ are independently hydrogen, hydrocarbyl, substituted hydrocarbyl, or boron containing moiety;
$R^{20}$ and $R^{21}$ are independently hydrogen, hydrocarbyl, or substituted hydrocarbyl; and
n is an integer of 1 or greater.

In a further aspect, the disclosure provides a process for preparing a compound of Formula (IIa). The process comprises contacting a compound of Formula (Ia) with a compound of Formula (IVa) in the presence of a transition metal catalyst and a chiral ligand to give the compound of Formula (IIa) according to the following reaction scheme:

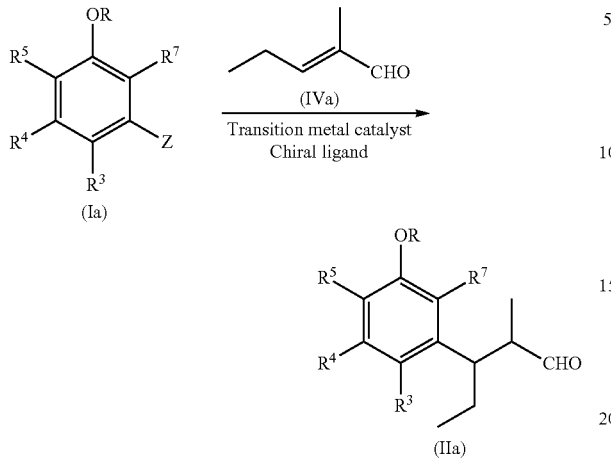

Reaction Scheme 1

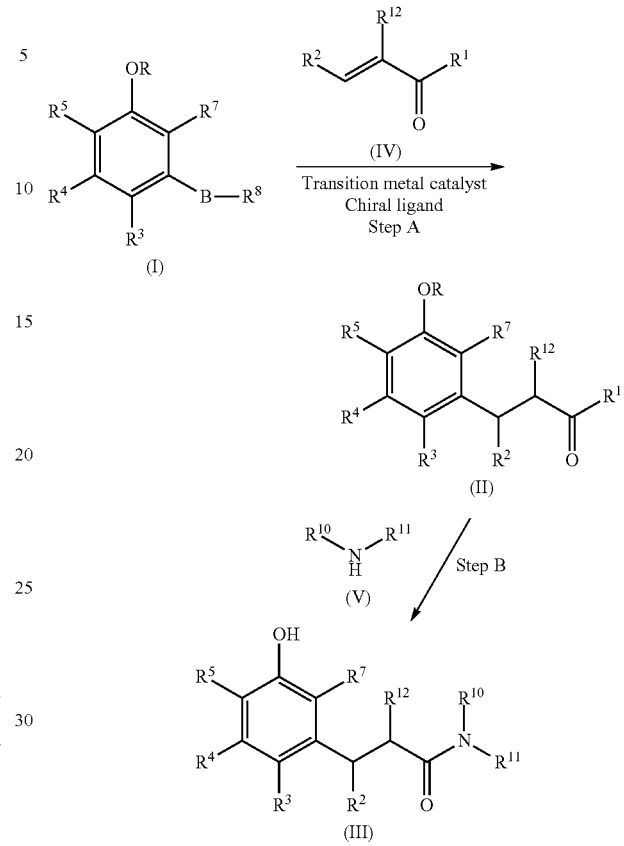

wherein:
Z is a boron containing moiety;
R is hydrogen, alkenyl, substituted alkenyl, aryl, or substituted aryl;
$R^3$, $R^4$, $R^5$, and $R^7$ are independently hydrogen, $OR^{20}$, $NR^{20}R^{21}$, $SR^{20}R^{21}$, halo, hydrocarbyl, or substituted hydrocarbyl; and
$R^{20}$ and $R^{21}$ are independently hydrogen, hydrocarbyl, or substituted hydrocarbyl.

Other features and iterations of the disclosure are described in more detail below.

DETAILED DESCRIPTION OF THE INVENTION

The present disclosure provides a concise process for preparing a substituted 3-substituted phenylalkylamines. In general, the process consists of a two-step process. The first step of the process involves a catalytic asymmetric 1,4-addition reaction of an α-substituted α,β-unsaturated carbonyl-containing compound with a phenyl boronic compound. Reductive alkylation as the second step provides a concise route to the 3-substituted phenylalkylamines. Alternatively, using a reduction procedure which performs reductive alkylation and removal of a protecting group provides a second concise route to 3-substituted phenyl alkyl amines. Surprisingly, these reaction sequences have been found useful in the total synthesis of tapentadol.

Compared to other conventional methods, the more concise routes presented provides a reduction in reaction steps, an increase in yield, increase in selectivity, and a time savings.

(I) A 2-Step Process for the Preparation of a Compound of Formula (III)

One aspect of the present disclosure provides a process for preparing a compound of Formula (III). The process comprises contacting a compound of Formula (I) with a compound of Formula (IV) in the presence of a transition metal catalyst and a chiral ligand to form a compound of Formula (II); and contacting the compound of Formula (II) with a secondary amine comprising Formula (V) to form the compound of Formula (III) according to the Reaction Scheme 1:

wherein:
R is hydrogen, alkenyl, substituted alkenyl, aryl, or substituted aryl;
$R^1$ is hydrogen, $OR^{20}$, $NR^{20}R^{21}$, $SR^{20}R^{21}$, hydrocarbyl, or substituted hydrocarbyl;
$R^2$ is chosen from hydrocarbyl and substituted hydrocarbyl;
$R^3$, $R^4$, $R^5$, and $R^7$ are independently chosen from hydrogen, $OR^{20}$, $NR^{20}R^{21}$, $SR^{20}R^{21}$, halo, hydrocarbyl, and substituted hydrocarbyl;
$R^8$ is

—O—$(CR^{13}R^{14})_n$—O—, or trihalo;
$R^{10}$ and $R^{11}$ are independently chosen from hydrocarbyl and substituted hydrocarbyl;
$R^{12}$ is chosen from hydrocarbyl or substituted hydrocarbyl;
$R^{13}$ and $R^{14}$ are independently hydrogen, hydrocarbyl, substituted hydrocarbyl, or $R^{10}$ and $R^{11}$ together may form a ring or ring system selected from carbocyclic, heterocyclic, aryl, heteroaryl, or combinations thereof;
$R^{20}$ and $R^{21}$ are independently chosen from hydrogen, hydrocarbyl, and substituted hydrocarbyl; and
n is an integer of 1 or greater.

In general, R is hydrogen, alkenyl, substituted alkenyl, aryl, or substituted aryl. In one embodiment, R may be hydrogen, substituted $C_1$-$C_{10}$ alkenyl, substituted $C_1$-$C_{10}$ alkenyl, aryl, or aryl($C_1$-$C_{10}$)alkyl. In certain embodiments, R may be hydrogen, allyl, benzyl, 4-methoxybenzyl, or phenethyl. In specific embodiments, R may be hydrogen or benzyl.

In some embodiments, $R^1$ may be hydrogen, alkyl, substituted alkyl, aryl, substituted aryl, hydroxyl, alkoxy, amino, mono substituted amino, disubstituted amino, thiol, or mono substituted thiol. In other embodiments, $R^1$ may be hydrogen, $C_1$-$C_{10}$ alkyl, or substituted $C_1$-$C_{10}$ alkyl, wherein alkyl may be linear, branched, or cyclic. In specific embodiments, $R^1$ may be hydrogen.

In other embodiments, $R^2$ may be alkyl, substituted alkyl, alkenyl, substituted alkenyl, alkynyl, substituted alkynyl, aryl, substituted aryl, alkylaryl, or substituted alkylaryl. In certain embodiments, $R^2$ may be $C_1$-$C_{10}$ alkyl or substituted $C_1$-$C_{10}$ alkyl. In some embodiments, $R^2$ may be methyl, ethyl, propyl, isopropyl, butyl, tertbutyl, pentyl, or hexyl. In specific embodiments, $R^2$ may ethyl.

In some embodiments, $R^3$, $R^4$, $R^5$, and $R^7$ may be independently hydrogen, alkyl, substituted alkyl, hydroxyl, alkoxy, substituted alkoxy, aryl, substituted aryl, alkylaryl, or substituted alkylaryl. In embodiments in which $R^3$, $R^4$, $R^5$, or $R^7$ independently may be $OR^{20}$, $NR^{20}R^{21}$, $SR^{20}R^{21}$, $R^{20}$ and $R^{21}$ independently are hydrogen, alkyl, substituted alkyl, aryl, or substituted aryl. In specific embodiments, each of $R^3$, $R^4$, $R^5$, and $R^7$ is hydrogen.

In certain embodiments, $R^8$ may be

wherein $R^{13}$ and $R^{14}$ are independently hydrogen, alky, substituted alkyl, aryl, substituted aryl, alkylaryl, substituted alkylaryl, or organoborane. In one iteration of this embodiment, each of $R^{13}$ and $R^{14}$ is hydrogen. In other embodiments, $R^8$ may be —O—$(CR^{13}R^{14})_n$—O—, wherein $R^{13}$ and $R^{14}$ are independently hydrogen, alkyl, substituted alkyl, aryl, substituted aryl, alkylaryl, substituted alkylaryl, or organoborane, and n is 1 or greater. In one iteration of this embodiments, each of $R^{13}$ and $R^{14}$ is methyl and n is 2. In still another embodiment, $R^8$ may be trihalo, such as, e.g., trifluoro.

In further embodiments, $R^{10}$ and $R^{11}$ independently may be $C_1$-$C_{10}$ alkyl or substituted $C_1$-$C_{10}$ alkyl, wherein alkyl is linear, branched, or cyclic. In certain embodiments, $R^{10}$ and $R^{11}$ independently may be methyl, ethyl, propyl, isopropyl, butyl, tertbutyl, pentyl, or hexyl. In specific embodiments, each of $R^{10}$ and $R^{11}$ may be methyl.

In some embodiments, $R^{12}$ may be $C_1$-$C_{10}$ alkyl or substituted $C_1$-$C_{10}$ alkyl, wherein alkyl is linear, branched, or cyclic. In certain embodiments, $R^{12}$ may be methyl, ethyl, propyl, isopropyl, butyl, tertbutyl, pentyl, or hexyl. In specific embodiments, each of $R^{12}$ may be methyl.

In exemplary embodiments, R may be hydrogen or benzyl; $R^1$ may be hydrogen; $R^2$ may be ethyl; each of $R^3$, $R^4$, $R^5$, and $R^7$ may be hydrogen; and each of $R^{10}$, $R^{11}$, and $R^{12}$ may be methyl.

(a) Step A of the 2-Step Process

Step A involves contacting a phenyl boronic compound of Formula (I) with a compound of Formula (IV) in the presence of a transition metal catalyst and a chiral ligand to form a compound of Formula (II). Contact between the phenyl boronic compound of Formula (I) and the compound of Formula (IV) during step A of the process entails an asymmetric 1,4-addition reaction.

(i) Phenyl Boronic Compound

The phenyl boronic acid comprising Formula (I) is detailed above. In some embodiments, R may be hydrogen, alkenyl, substituted alkenyl, aryl, or substituted aryl, each of $R^3$, $R^4$, $R^5$, and $R^7$ may be hydrogen, alkyl, or substituted alkyl, and $R^{13}$ and $R^{14}$ may be hydrogen or alkyl if present. In certain embodiments, R may be hydrogen, substituted alkyl, or arylalkyl, each of $R^3$, $R^4$, $R^5$, and $R^7$ may be hydrogen, and $R^{13}$ and $R^{14}$ may be hydrogen or alkyl if present. In preferred embodiments in which R is hydrogen or benzyl and each of $R^3$, $R^4$, $R^5$, and $R^7$ is hydrogen, the compound of Formula (I) may be 3-hydroxyphenylboronic acid, 3-hydroxyphenyl trifluoroborate, 3-hydroxyphenylboronic acid pinacol ester, 3-hydroxyphenylboronic ester, 3-benzyloxyphenylboronic acid, 3-benzyloxyphenyl trifluoroborate, 3-benzyloxyphenylboronic acid pinacol ester, or 3-benzyloxyphenylboronic ester. Also, a compound of Formula (I) may be derived from mono, bis, or tris substituted 3-hydroxyphenylboroxine, or 3-benzyloxyphenylboroxine, or an acceptable salt thereof.

(ii) α,β-Unsaturated Carbonyl Compound

The α,β-unsaturated carbonyl compound of Formula (IV) is detailed above. In some embodiments, $R^1$, $R^2$, and $R^{12}$ may be hydrogen, alkyl, or substituted alkyl. In certain embodiments, $R^1$ may be hydrogen and $R^2$ and $R^{12}$ may be alkyl or substituted alkyl. In preferred embodiments in which $R^1$ is hydrogen, $R^2$ is ethyl, and $R^{12}$ is methyl, i.e., the compound may be trans-2-methyl-2-pentenal.

In general, the molar ratio of the compound of Formula (I) to the compound of Formula (IV) may range from about 1:0.5 to about 1:6.0. In various embodiments, the molar ratio of the compound of Formula (I) to the compound of Formula (IV) may range from about 1:0.5 to about 1:0.6, 1:0.6 to about 1:0.7, 1:0.7 to about 1:0.8, 1:0.8 to about 1:0.9, from about 1:0.9 to 1:1, from about 1:1 to about 1:1.2, from about 1:1.2 to about 1:1.4, from about 1:1.4 to about 1:1.6, from about 1:1.6 to about 1:1.8, from about 1:1.8 to about 1:2, from about 1:2 to 1:4, or from about 1:4 to 1:6. In an exemplary embodiment, the molar ratio of the compound of Formula (I) to the compound of Formula (IV) may range from about 1:1.0 to about 1:1.4.

(iii) Transition Metal Catalyst

A wide variety of transition metal catalysts may be used in the process to catalyze the 1,4-addition of step A. As used herein, the term "transition metal catalyst" refers to a transition metal element, transition metal salt, or a transition metal complex. In some embodiments, the transition metal may be iridium, iron, nickel, osmium, palladium, platinum, ruthenium, or rhodium. In one exemplary embodiment, the transition metal may be rhodium, palladium, or ruthenium. A skilled artisan appreciates that the oxidation state of transition metal may vary, and may be, for example, (0), (I), (II), (III), (IV), (V), (VI) or (VII). For example, non-limiting examples of suitable transition metals include ruthenium (II), ruthenium (III), ruthenium (IV), osmium (II), osmium (III), osmium (IV), rhodium (I), rhodium (III), iridium (III), iridium (IV), palladium (II), palladium (IV), platinum (II), and platinum (IV). In an exemplary embodiment the transition metal may be rhodium (I).

In some embodiments, the transition metal catalyst may be the transition metal element itself. For example, the transition metal element may be a powder or a sponge, such as, e.g., ruthenium powder, rhodium powder, ruthenium sponge, rhodium sponge, palladium sponge, and so forth. Alternatively, the transition metal element may be rhodium black, ruthenium black, palladium black, etc. In still other embodiments, the transition metal element may be immobilized on a solid surface or support. Suitable examples include, but are not limited to, ruthenium on carbon, rhodium on carbon, palladium on carbon, ruthenium on alumina, rhodium on alumina, platinum on alumina, palladium on alumina, rhodium on silica, palladium on silica, palladium on charcoal, palladium on pumice, and so forth.

In other embodiments, the transition metal catalyst may be a transition metal salt. Non-limiting examples of suitable salts include acetates, acetyacetonates, alkoxides, butyrates, carbonyls, dioxides, halides, hexonates, hydrides, mesylates, octanates, nitrates, nitrosyl halides, nitrosyl nitrates, sulfates, sulfides, sulfonates, phosphates, trifluoromethanesulfonates, trimethylacetates, tosylates, and combinations thereof. Non-limiting examples of suitable transition metal salts include $RuCl_3$, $RuBr_3$, $Ru(CF_3SO_3)_2$, $Ru_2(SO_4)_3$, $Ru(NO_3)_3$, $Ru(OAc)_3$, $PdCl_2$, $Pd(OAc)_2$, $RhCl_3$, $RhBr_3$, $Rh_2(SO_4)_3$, $(Rh(CO_2)Cl)_2$, $Rh_2(SO_4)_3$, $Rh_2(OAC)_4$, $IrCl_3$, and $OsCl_3$. The transition metal salt may be soluble (i.e., homogeneous). Alternatively, the transition metal salt may be immobilized on a solid support (i.e., heterogeneous). The transition metal salt may be immobilized on the solid support via noncovalent or covalent bonds. In some embodiments, the solid support may be an inorganic material. Suitable inorganic materials include silicas, alumina, titania, carbondium, zirconia, activated charcoal, zeolites, clays, polymers, ceramics, and activated carbon. Suitable silicas include silicon dioxide, amorphous silica, and microporous or mesoporous silicas. In other embodiments, the solid support may be a polymer. The polymer may be a natural polymer, a synthetic polymer, a semi-synthetic polymer, or a copolymer. Non-limiting examples of polymers include agarose, cellulose, nitrocellulose, methyl cellulose, polyacrylic, polyacrylamide, polyacrylonitrile, polyamide, polyether, polyester, polyethylene, polystyrene, polysulfone, polyvinyl chloride, polyvinylidene, methacrylate copolymer, and polystyrene-vinyl chloride copolymer.

In further embodiments, the transition metal catalyst may be a transition metal complex. For example, the transition metal catalyst may be a rhodium complex, a palladium complex, or a ruthenium complex. In general, a transition metal complex comprises the transition metal and 4, 5, or 6 coordinate species with oxidation states ranging from 0 to 8. The complexes may be ionic, or the complexes may comprise covalently bound ligands and counter ions. Alternatively, the complexes may comprise a mixture of ionic and covalent bonds between the metal, ligand(s), and/or counter ion(s). The ligand may be monodentate or polydentate. Non-limiting examples of suitable ligands include arene ligands, olefin ligands, alkyne ligands, heterocycloalkyl ligands, heteroaryl ligands, alkyl ligands, cyclopentadienyl ligands, hydride ligands, amine ligands, carbonyl ligands, nitrogen donor ligands, phosphorous donor ligands, oxygen donor ligands, and so forth. The ligand may also be a solvent such as, e.g., DMSO, methanol, methylene chloride, tetrahydrofuran, acetone, ethanol, pyridine, or a tetraalkylammonia compound. Suitable counter ions include, but are not limited to, halides, $BF_4^-$, $PF_6^-$, $ClO_4^-$, $CHO_2^-$, $CF_3SO_3^-$, $CH_3CO_2^-$, $ArCO_2^-$, $CH_3SO_3^-$, p-tolyl$SO_3^-$, $HSO_4^-$, $H_2PO_4^-$, and hydrocarbyl anions. Numerous transition metal complexes are detailed in "Transposition of Allylic Alcohols into Carbonyl Compounds Mediated by Transition Metal Complexes" by Uma et al., Chem. Rev. 103: 27-51 (2003).

The transition metal complex may be soluble (i.e., homogeneous). Alternatively, the transition metal complex may be immobilized on a solid support (i.e., heterogeneous). The transition metal complex may be immobilized on the solid support via noncovalent or covalent bonds. Examples of suitable solid supports are presented above.

Exemplary transition metal catalysts include, but are not limited to, [RhCl($C_2H_4$)$_2$]$_2$, [RuCl($C_2H_4$)$_2$]$_2$, [PdCl($C_2H_4$)$_2$]$_2$, [PtCl($C_2H_4$)$_2$]$_2$, [RhBr($C_2H_4$)$_2$]$_2$, [RuBr($C_2H_4$)$_2$]$_2$, [PdBr($C_2H_4$)$_2$]$_2$, [PtBr($C_2H_4$)$_2$]$_2$, (1,5-cyclooctadiene)bis(triphenyl-phosphine)rhodium(I) hexafluorophosphate, (acetylacetonato)(1,5-cyclooctadiene)rhodium(I), (acetylacetonato)(norbornadiene)rhodium(I), [1,4-bis(diphenylphosphino)butane](1,5-cyclooctadiene)rhodium(I) tetrafluoroborate, acetylacetonatobis(ethylene)rhodium(I), bicyclo[2.2.1]hepta-2,5-diene-rhodium(I) chloride, bis(1,5-cyclooctadiene)rhodium(I) tetrafluoroborate, bis(1,5-cyclooctadiene)rhodium(I) tetrakis[bis(3,5-trifluoromethyl)phenyl]borate, bis(1,5-cyclooctadiene)rhodium(I) trifluoromethanesulfonate, bis(acetonitrile)(1,5-cyclooctadiene)rhodium(I)tetrafluoroborate, bis(norbornadiene) rhodium(I) tetrafluoroborate, bis(triphenylphosphine)rhodium(I) carbonyl chloride, bis[rhodium(α,α,α',α'-tetramethyl-1,3-benzenedipropionic acid)], chloro(1,5-hexadiene)rhodium(I), chlorobis(cyclooctene)rhodium(I), dicarbonyl(pentamethylcyclopentadienyl)rhodium(I), hydridotetrakis(triphenylphosphine)rhodium(I), hydroxy(cyclooctadiene)rhodium(I), methoxy(cyclooctadiene)rhodium(I), rhodium(II) heptafluorobutyrate, rhodium(II) hexanoate, rhodium(II) octanoate, rhodium(II) trifluoroacetate, rhodium(II) trimethylacetate, rhodium(II) triphenylacetate, rhodium(III) acetylacetonate, rhodium(III) phosphate, tris(triphenylphosphine)rhodium(I) carbonyl, tris(triphenylphosphine)rhodium(I), (2-methylallyl)palladium(II) chloride, (ethylenediamine)palladium(II) chloride, [1,2-bis(dicyclohexylphosphino)ethane] palladium(II) chloride, [2,6-bis[(di-1-piperidinylphosphino)amino]phenyl]palladium(II) chloride, 1,2-bis(phenylsulfinyl)ethane palladium(II) acetate, 1,4-bis(diphenylphosphino) butane-palladium(II) chloride, allylchloro[1,3-bis(2,4,6-trimethylphenyl)imidazol-2-ylidene]palladium(II), bis(benzonitrile) palladium(II) chloride, bis(dibenzylideneacetone) palladium(O), bis(triphenylphosphine)palladium(II) diacetate, bis(triphenylphosphine) palladium(II) dichloride, bis(tri-tert-butylphosphine)palladium(O), bis[(dicyclohexyl)(4-dimethylaminophenyl)phosphine] palladium(II) chloride, bromo(tri-tert-butylphosphine)palladium(I), chloro(2-dicyclohexylphosphino-2',4',6'-triisopropyl-1,1'-biphenyl)[2-(2-aminoethyl)phenyl)]palladium(II), chloro-(2-dicyclohexylphosphino-2',6'-diisopropoxy-1,1'-biphenyl)[2-(2-aminoethyl)phenyl]palladium(II), chloro[2-(dicyclohexylphosphino)-3,6-dimethoxy-2',4',6'-triisopropyl-1,1'-biphenyl][2-(2-aminoethyl)phenyl] palladium(II), chloro[2-(di-tert-butylphosphino)-2',4',6'-triisopropyl-1,1'-biphenyl][2-(2-aminoethyl)phenyl)] palladium(II), dichloro(1,5-cyclooctadiene) palladium(II), dichlorobis(tricyclohexylphosphine)palladium(II), di-μ-chlorobis[5-chloro-2-[(4-chlorophenyl)(hydroxyimino-κN)methyl]phenyl-κC]palladium, di-μ-chlorobis[5-hydroxy-2-[1-(hydroxyimino-κN)ethyl]phenyl-κC]palladium(II), N-methylimidazolium palladium(II), palladium(II) hexafluoroacetylacetonate, palladium(II)[1,3-bis(diphenylphosphino)propane]-bis(benzonitrile)-bis-tetrafluoroborate; tetrakis(acetonitrile)palladium(II), tetrakis(triphenylphosphine)palladium(O), tetrakis[triphenylphosphine]palladium(O), (1,5-cyclooctadiene)dimethylplatinum(II), (2,2'-bipyridine)dichloroplatinum(II), (N,N,N'- trimethylethylenediamine)platinum(II) chloride, ammonium hexachloroplatinate(IV), ammonium tetrachloroplatinate (II), bis(tri-tert-butylphosphine)platinum(0), chloro(2,2':6',2"-terpyridine)platinum(II) chloride, cis-bis(acetonitrile)dichloroplatinum(II), cis-diammineplatinum(II) dichloride, cis-dichlorobis(diethyl sulfide)platinum(II), cis-dichlorobis(pyridine)platinum(II), cis-dichlorobis(triethylphosphine)platinum(II), cis-dichlorobis(triphenylphosphine) platinum (II), dibromo(1,5-cyclooctadiene)platinum(II), dichloro(1,10-phenanthroline) platinum(II), dichloro(1,2-diaminocyclohexane)platinum(II), dichloro(1,5-cyclooctadiene)platinum(II), dichloro(2,2':6',2"-terpyridine)platinum(II) dihydrate, dichloro(dicyclopentadienyl)platinum(II), dichloro(ethylenediamine)platinum(II), dichloro(norbornadiene)platinum(II), dichlorobis(dimethyl sulfide)platinum(II), dichlorobis(ethylenediamine)platinum (II), ethylenebis(triphenylphosphine)platinum(O), oxalato-bis(triethylphosphine)platinum(II), platinum(0)-1,3-divinyl-1,1,3,3-tetramethyldisiloxane, platinum(0)-2,4,6,8-tetramethyl-2,4,6,8-tetravinylcyclo-tetrasiloxane, potassium hexachloroplatinate(IV), potassium tetrachloroplatinate(II), potassium tetracyanoplatinate(II), tetrakis(triphenylphosphine)platinum(0), trans-dichlorobis(triethylphosphine) platinum(II), trans-dichlorobis(triphenylphosphine) platinum(II), trimethyl(methylcyclopentadienyl)platinum(IV). In an exemplary embodiment, the transition metal catalyst may be $[RhCl(C_2H_4)_2]_2$.

In other embodiments, the transition metal catalyst may be a complex comprising the transition metal and a tertiary phosphite, a tertiary phosphine, or a tertiary phosphine halide as detailed in U.S. Pat. Nos. 7,321,038, 7,399,858, and 7,323,565, each of which is incorporated herein with reference to the identity and synthesis of the transition metal catalyst. Non-limiting examples of phosphine containing complexes include $(phosphine)_xPdCl_2$, $(PPh_3)_4Pd$, $RuCl_2(PPh_3)_3$, $RuCl_2(PPh_3)_4$, $RuH_2(PPh_3)_4$, and $RhCl(PPh_3)_3$. In yet another embodiment, transition metal catalyst may be a complex comprising the transition metal and an amine phosphine complex as described in U.S. Pat. No. 7,399,859, which is incorporated herein reference to the identity and synthesis of the transition metal catalyst. Suitable chiral phosphine ligands which may form transition metal complexes are listed below in Section (I)(a)(iv).

The molar ratio of the compound of Formula (I) to the transition metal catalyst may vary depending, for example, on the nature of the catalyst. In general, the molar ratio of the compound of Formula (I) and the transition metal catalyst complex will range from about 1:0.0001 to about 1:0.1. In certain embodiments, the molar ratio of the compound of Formula (I) to the transition metal catalyst may range from about 1:0.0001 to about 1:0.001, from about 1:0.001 to about 1:0.005, from about 1:0.005 to about 1:0.025, or from about 1:0.025 to about 0.1. In one embodiment, the molar ratio of the compound of Formula (I) to the transition metal catalyst may range from about 1:0.005 to about 1:0.01. In another embodiment, the molar ratio of the compound of Formula (I) to the transition metal catalyst may range from about 1:0.0005 to about 1:0.005.

(iv) Chiral Ligand

Chiral ligands may be any organic ligand that can complex with a catalytic metal and has at least one stable chiral center, and exemplarily two chiral centers. Phosphines, nitrogen-containing compounds and dienes are examples of classes of compounds that may function as chiral ligands.

Chiral phosphine ligands include, but are not limited to, (3,5-dioxa-4-phospha-cyclohepta[2,1-a;3,4-a']dinaphthalen-4-yl)dimethylamine (MONOPHOS), (3,5-dioxa-4-phospha-cyclohepta[2,1-a;3,4-a']dinaphthalen-4-yl)morpholine (MorfPhos), (3,5-dioxa-4-phospha-cyclohepta[2,1-a;3,4-a']dinaphthalen-4-yl)piperidine (PipPhos), (5,6),(5',6)-bis(ethylenedioxy)-biphenyl-2,2'-diyl]-bis(diphenylphosphine) (Synphos), (6,6'-dimethyoxybiphenyl-2,2'-diyl)bis(diphenylphosphine) (BIPHEMP), 1-(2-dipheylphospino-1-naphthyl)isoquinoline (Quinap), 1-[(dinaphtho[2,1-d:1',2'-f][1,3,2]dioxaphosphepin-4-yloxy)propan-2-yl]-3-phenylurea (UREAPhos), 1-tert-butoxycarbonyl-4-diphenylphosphino-2(diphenylphosphinomethyl)pyrrolidine (BPPM), 1,1'-di-t-butyl-[2,2']-diphospholane (TANGPHOS), 1,13-bis(diphenylphosphino)-7,8-dihydro-6H-dibenzo[f,h][1,5]dioxonin (TUNEPHOS), 1,2-bis(diphenylphosphino)propane (PROPHOS), 1,2-bis(phospholano)benzene (DuPHOS), 1,2-bis(phospholano)ethane (BPE), 1,2-bis(t-butylmethylphosphino)benzene (BenzP*), 1,2-bis[(2-methoxyphenyl)(phenylphosphino)]ethane (DIPAMP), 1,2-bis[2,5-dimethyl-3,4-dihydroxyphospholano]benzene (ROPHOS), 10,11,12,13-tetrahydrodiindeno[7,1-de:1',7'-fg][1,3,2]dioxaphosphocin-5-bis[1-phenylethyl]amine (SIPHOS-PE), 10,11,12,13-tetrahydrodiindeno[7,1-de:1',7'-fg][1,3,2]dioxaphosphocin-5-dimethylamine (SIPHOS), 10,11,12,13-tetrahydrodiindeno[7,1-de:1',7'-fg][1,3,2]dioxaphosphocin-5-phenoxy (ShiP), 2-(diphenylphosphino)-2'-methoxy-1,1'-binaphthyl (MOP), 2-(diphenylphosphinomethyl)-4-(dicyclohexylphosphino)-N-(t-butoxycarbonyl)pyrrolidine (BCPM), 2-(diphenylphosphinomethyl)-4-(dicyclohexylphosphino)-N-methyl-1-pyrrolidinecarboxamide (MC-CPM), 2-(diphenylphosphinomethyl)-4-(diphenyl-phosphino)-N-(t-butoxycarbonyl)pyrrolidine (BPPM), 2-(diphenylphosphinomethyl)-4-(diphenylphosphino)pyrrolidine (PPM), 2-amino-1-phenylpropyldiphenylphosphine, 2,2'-bis(diphenylphosphino)-1,1'-biphenyl (DIPHEP), 2,2'-bis(N-diphenylphosphinoamino)-5,5',6,6',7,7',8,8'-octahydro-1,1'-binaphthyl (CTH-BINAM), 2,2'-bis[bis(3,5-dimethylphenyl)phosphino]-4,4',6,6'-tetramethoxybiphenyl (Xyl-Garphos) 2,3-bis(diphenylphosphino)-bicyclo[2.2.1]hept-5-ene (NORPHOS), 2,3-O-isopropylidene-2,3-dihydroxy-1,4-bis(diphenylphosphino)butane (DIOP), 2,4-bis(diphenylphosphino) pentane (BDPP), 4,12-bis(diphenylphosphino)-[2.2]-paracyclophane (PHANEPHOS), 4,4'-di-t-butyl-4,4',5,5'-tetrahydro-3,3'-bi-3H-dinaphtho[2,1-c:1',2'-e]phosphepin (BINAPINE), 4,5-bis(diphenylphosphinomethyl)-2,2-dimethyl-1,3-dioxolane (DIOP), 5,5'-bis[di(3,5-di-t-butyl-4-methoxyphenyl)phosphino]-4,4'-bi-1,3-benzodioxole (DTBM-STEGPHOS), 5,6,10,11,12,13-hexahydro-5-phenyl-4H-diindeno[7,1-cd:1,7-ef]phosphocin (SITCP), 6,6'-[(3,3'-di-t-butyl-5,5'-dimethoxy-1,1'-biphenyl-2,2'-diyl)bis(oxy)]bis(dibenzo[d,f][1,3,2]dioxaphosphepin) (DIPHEPHOS), 6,6'-{[1,3-dimethyl-1,3-propanediyl]bis(oxy)}bis[4,8-bis(t-butyl)-2,10-dimethoxy-bibenzo[d,f][1,3,2]dioxaphosphepin] (Chiraphite), 7,7'-bis(diphenylphosphino)-2,2',3,3'-tetrahydro-1,1'-spirobiindane (SDP), bis-(1,2-diphenylphosphino)propane (PROPHOS), bis(diphenyl-phosphino)butane (CHIRAPHOS), bis(diphenylphosphino) dicyclopentane (BICP), bis(diphenylphospino)-1,1'-binaphthyl (BINAP), Nidinaphtho[2,1-d:1',2'-f][1,3,2]dioxaphosphepin-4-yl]-1,1,1-neomenthyldiphenylphosphine (NMDPP), and trifluoromethanesulfonamide (METAMORPhos).

Chiral nitrogen-containing ligands include, but are not limited to, α,α-diphenyl-2-pyrrolidinemethanol (DPP), and α,α-diphenyl-2-pyrrolidinemethanol trimethylsilyl ether (DPPT), 1,1-bis(4-methoxyphenyl)-3-methyl-1,2-butanediamine (DAIPEN), 1,2-bis(2-hydroxyphenyl)ethylenediamine (DPEN), 1,2-bis(4-cyanophenyl)ethylenediamine, 1,2-bis(4-dimethylaminophenyl) ethylenediamine, 1,2-bis (4-dimethylaminophenyl) ethylenediamine, 1,2-bis(4-nitrophenyl)ethylenediamine, 1,2-cyclohexanediamino-N,N'-bis (3,5-di-t-butylsalicylidene) (Jacobsen Ligand), 1,2-diaminocyclohexane (DACH), 1,2-diphenylethylenediamine, 2-(4-t-butyl-4,5-dihydro-oxazol-2-yl)propan-2-ol, 2-(methanamine)-1H-benzimidazole (BIMAH), 2,2'-bipyrrolidine, 2,2'-diamino-1,1'-binaphthyl, 2,3-bis(tert-butylmethylphosphino)quinoxaline, 2,6-bis[(3a, 8a-dihydro-8H-indeno[1,2-d]oxazolin-2-yl]pyridine (Indenyl-PYBOX), 2,6-bis[(-4-(i-propyl)-2-oxazolin-2-yl]pyridine (i-Pr-PYBOX), 7,7-bis[(phenyl)oxazol-2-yl)]-2,2,3,3-tetrahydro-1,1-spirobiindane (SpiroBOX), chichonidine, cis-1-aminoindan-2-ol, dihydroquinidine (DHQD), dihydroquinine (DHQ), N,N'-1,2-diaminocyclohexanediylbis(2-pyridine-carboxamide), N,N'-bis(2-pyridylmethyl]-2,2'-bipyrrolidine (PDP), N,N'-1,2-diaminocyclohexanediylbis(2-pyridinecarboxamide) (DACH-pyridyl), quinine and sparteine.

Chiral dienes may include monocyclic dienes and bicyclic dienes. An example of a monocyclic diene is diphenylcyclooctadiene (Ph-cod*). Bicyclic dienes based on a bicyclo [2.2.1]hepta-2,5-diene skeleton (nbd*) include, but are not limited to, 2,5-dibenzylbicyclo[2.2.1]hepta-2,5-diene (Bn-nbd*), 2,5-dimethylbicyclo[2.2.1]hepta-2,5-diene (Me-nbd*), 2,5-diphenylbicyclo[2.2.1]hepta-2,5-diene (Ph-nbd*), and 2,5-bis(2,4,6-trimethylbenzyl)-bicyclo[2.2.1] hepta-2,5-diene (Bn-nbd*) (Mm-nbd*). Bicyclic dienes based on a bicyclo[2.2.2]octa-2,5-diene skeleton (bod*) include, but are not limited to, 2,5-diphenylbicyclo[2.2.2] octa-2,5-diene (Ph-bod*), 2,5-diphenylbicyclo[2.2.2]octa-2, 5-diene (Ph-bod*) and 2,5-dibenzylbicyclo[2.2.2]octa-2,5-diene (Bn-bod*). Bicyclic dienes based on a bicyclo[3.3.1] nona-2,6-diene skeleton (bnd*) include, but are not limited to, 2,6-diphenylbicyclo[3.3.1]nona-2,6-diene (Ph-bnd*) and 2,6-ditolylbicyclo [3.3.1]nona-2,6-diene (Tol-bnd*). Bicyclic dienes based on a bicyclo[3.3.2]deca-2,6-diene (bdd*) skeleton include, for example, 2,6-diphenylbicyclo[3.3.2] deca-2,6-diene (Ph-bdd*). Other chiral ligands may be identified, for example, in Aldrichimica Acta, Vol. 42, No. 2 (2009), which is hereby incorporated by reference with respect to the listing of ligands. In an exemplary embodiment, the chiral ligand may be 2,5-diphenylbicyclo[2.2.2] octa-2,5-diene (Ph-bod*). The 2,5-diphenylbicyclo[2.2.2] octa-2,5-diene (Ph-bod*) may be chosen from (1S, 4R)-2, 5-diphenylbicyclo[2.2.2]octa-2,5-diene; (1S, 4S)-2,5-diphenylbicyclo[2.2.2]octa-2,5-diene; (1R, 4S)-2,5-diphenylbicyclo[2.2.2]octa-2,5-diene; and (1R, 4R)-2,5-diphenylbicyclo[2.2.2]octa-2,5-diene.

Any chiral ligands mentioned above may be derivatized, for example, with one or more alkyl groups, such as methyl or ethyl, or one or more aryl groups, such as phenyl, benzyl, tolyl, or methoxyphenyl. Other examples of chiral phosphine, nitrogen-containing and diene ligands may be found in Catalytic Asymmetric Synthesis, Second Edition, edited by I. Ojima, Wiley-VCH, Inc. (2000); M. McCarthy and P. J. Guiry, "Axially chiral bidentate ligands in asymmetric catalysis," Tetrahedron, 57:3809-3844 (2001); and W. Tang and Z. Zhang, "New Chiral Phosphorous Ligands for Enantioselective Hydrogenation," Chemical Reviews, 103: 3029-3069 (2003). In addition to the above-mentioned dienes that possess an intrinsic stable chirality, some achiral dienes may also exhibit chirality upon coordination to a transition metal.

The weight ratio of the transition metal catalyst to the chiral ligand can and will vary. In general, the weight ratio of the transition metal catalyst to the chiral ligand will range from about 1:0.5 to about 1:2. In certain embodiments, the weight ratio of the transition metal catalyst to the chiral ligand may range from about 1:0.5 to about 1:0.75, from about 1:0.75 to about 1:1.0, from about 1:1.0 to about 1:1.5, or from about 1:1.5 to about 1:2.0. In an exemplary embodiment, the weight ratio of the transition metal catalyst to the chiral ligand may be about 1:1.5.

(v) Optional Amine Addition

In some embodiments, the reaction mixture may further comprise an amine. Depending on the starting substrates, the transition metal catalyst, and the chiral ligand, the amine may be a secondary amine, a tertiary amine, or combination thereof. The amine may be chiral or achiral. Non-limiting examples of suitable secondary amines include ethyl methyl amine, dimethyl amine, diethyl amine, dicyclohexyl amine, methyl cyclohexyl amine, phenyl ethyl amine, dibenzyl amine, methyl benzyl amine, ethyl benzyl amine, cyclohexyl phenyl amine, dibutyl amine, ditertiarybutyl amine, dipropyl amine, dipentylamine, dicyclohexyl amine, piperidine, 2-methylpiperidine, 2,5-dimethylpiperidine, 2,6-dimethylpiperidine, piperazine, 2-methylpiperazine, 2,6-dimethylpiperazine, and morpholine. Non-limiting examples of suitable tertiary amines include trimethylamine, triethylamine, diisopropylethylamine, tripropylamine, tributylamine, 4-methylmorpholine, 4-ethylmorpholine, N-methylpyrrolidine, N-methylpiperidine, 1,8-diazabicyclo[5.4.0]undec-7-ene (DBU), pyrazine, 4-dimethylaminopyridine, pyridine, and 2,6-lutidine. Non-limiting examples of chiral secondary amines (R)-α-methylbenzylamine, (S)-α-methylbenzylamine, (R)-α,α-diphenyl-2-pyrrolidinemethanol (DPP), (S)-α, α-diphenyl-2-pyrrolidinemethanol (DPP), (R)-α,α-diphenyl-2-pyrrolidinemethanol trimethylsilyl ether (DPPT) and (S)-α,α-diphenyl-2-pyrrolidinemethanol trimethylsilyl ether (DPPT).

The molar ratio of the compound of Formula (I) to the amine may vary depending, for example, on the substrate being used, the nature of the catalyst, and the solvent of the process. In general, the molar ratio of the compound of Formula (I) and the amine will range from about 1:0.01 to about 1:1.0. In certain embodiments, the molar ratio of the compound of Formula (I) to the amine may range from about 1:0.01 to about 1:0.025, from about 1:0.025 to about 1:0.05, from about 1:0.05 to about 1:0.10, from about 1:0.10 to about 1:0.5, or from about 1:0.5 to about 1:1.0. In one embodiment, the molar ratio of the compound of Formula (I) to the amine may range from about 1:0.05 to about 1:0.5. In a further embodiment, the molar ratio of the compound of Formula (I) to the amine may be about 1:0.2.

(vi) Optional Proton Acceptor

The reaction mixture, as detailed herein, may also comprise a proton acceptor. The proton acceptor will vary depending on the starting substrates, the transition metal, and the chiral ligand. Non-limiting examples of suitable proton acceptors include sodium hydroxide, potassium hydroxide, calcium hydroxide, barium hydroxide, cesium carbonate, sodium bicarbonate, potassium bicarbonate, sodium carbonate, potassium carbonate, sodium borate, sodium dihydrogen phosphate, disodium hydrogen phosphate, sodium methoxide, sodium tert-butoxide, and potassium tert-butoxide.

The molar ratio of the compound of Formula (I) to the proton acceptor may vary depending, for example, on the substrate being used, the nature of the catalyst, and the solvent of the process. In general, the molar ratio of the compound of Formula (I) and the proton acceptor will range from about 1:0.001 to about 1:2.0. In certain embodiments, the molar ratio of the compound of Formula (I) to the proton acceptor may range from about 1:0.001 to about 1:0.01, from about 1:0.01 to about 1:0.03, from about 1:0.03 to about 1:0.1, from about 1:0.1 to about 1:0.3, from about 1:0.3 to about 1:1.0, or from about 1:1.0 to about 1:2.0. In one embodiment, the molar ratio of the compound of Formula (I) to the proton acceptor may range from about 1:0.01 to about 1:0.25.

(vii) Solvent

The reaction mixture, as detailed herein, may also comprise a solvent. The solvent can and will vary depending on the starting substrates, the transition metal catalyst, and the chiral ligand used in the process. The solvent may be a polar protic solvent, a polar aprotic solvent, a non-polar solvent, or combinations thereof. Suitable examples of polar protic solvents include, but are not limited to, water; alcohols such as methanol, ethanol, isopropanol, n-propanol, isobutanol, n-butanol, s-butanol, t-butanol, and the like; diols such as ethylene glycol, propylene glycol; polyols such as glycerol, mannitol, sorbitol; organic acids such as formic acid, acetic acid, and so forth; amines such as trimethylamine, or triethylamine, and the like; amides such as formamide, acetamide, and so forth; and combinations of any of the above. Non-limiting examples of suitable polar aprotic solvents include acetonitrile, dichloromethane (DCM), diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, methylene chloride, nitrobenzene, nitromethane, propionitrile, sulfolane, tetramethylurea, tetrahydrofuran (THF), 2-methyltetrahydrofuran, trichloromethane, and combinations thereof. Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof. In one exemplary embodiment, the solvent may be a combination of polar solvents. For example, the solvent may be a combination of water, and an alcohol, such as methanol. The combination of water/methanol may be in any volume to volume ratio, ranging from 99:1 to 1:99, for example, including, 75:25, 50:50, 25:75, and at values between the listed values. In one embodiment, the combination of water/methanol may be about 40/60. In another embodiment, the combination of water/methanol may be about 33/67.

In general, the volume to weight ratio of the solvent to the compound of Formula (I) will range from about 1.0:1 to about 50:1. In various embodiments, the volume to weight ratio of the solvent to the compound of Formula (I) may range from about 1.0:1 to about 2:1, from about 2:1 to about 5:1, from about 5:1 to about 25:1, or from about 25:1 to about 50:1. In an exemplary embodiment, the volume to weight ratio of the solvent to the compound of Formula (I) may range from about 2:1 to about 10:1.

The pH of the reaction mixture may be adjusted to optimize activity of the transition metal catalyst. In general, the optimal pH will vary depending upon the nature of the transition metal catalyst. A person of skill in the art will know how to determine the optimal pH level for the transition metal catalyst of interest.

(viii) Reaction Conditions

In general, the reaction of step A will be conducted at a temperature that ranges from about −10° C. to about 80° C. In various embodiments, the temperature of the reaction may range from about −10° C. to about 0° C., 0° C. to about 10° C., 10° C. to about 20° C., from about 20° C. to about 30° C., from about 30° C. to about 40° C., from about 40° C. to about 60° C., or from about 60° C. to about 80° C. In one embodiment, the reaction may be conducted at temperature that ranges from about 20° C. to about 50° C. or from about 35° C. to about 45° C. In another embodiment, the temperature of the reaction may be about room temperature (~23° C.). The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as chromatography (e.g., HPLC). The duration of the reaction can and will vary depending many factors, such as the starting substrates, the solvent of the reaction, and the temperature used in the process. The duration of the reaction may range from about 5 minutes to about 48 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours, from about 24 hours to about 36 hours, or from about 36 hours to about 48 hours. In one embodiment, the reaction may be allowed to proceed for about 0.5 hour to about 2 hours. In another embodiment, the reaction may be allowed to proceed for about 24 hours to 36 hours. In this context, a "completed reaction" generally means that the reaction mixture contains a significantly diminished amount of the compound of Formula (I). Typically, the amount of the compound of Formula (I) remaining in the reaction mixture at the end of the reaction may be less than about 10%, less than about 5%, or less than about 2%.

The compound of Formula (II) may have a yield of at least about 25%. In various embodiments, the compound of Formula (II) may have a yield of at least about 25%, a yield of at least about 30%, a yield of at least about 40%, a yield of at least about 50%, at least about 60%, at least about 65%, at least about 70%, at least about 75%, at least about 80%, at least about 85%, at least about 90%, at least about 95%, or at least about 99%.

The compound of Formula (II) may have a percent of diastereomeric excess (DE %) greater than 20%, at least about 30%, at least about 40%, at least about 50%, at least about 60%, at least about 70%, at least about 80%, at least about 90%, at least about 95%, at least about 99%, or at least about 99.5%. The compound of Formula (II) may have (2R, 3R) or (2S,3R) stereochemistry. In specific embodiments, the compound of Formula (II) may have (2R, 3R) stereochemistry. For the compound of Formula (II) where R is hydrogen and $R^1$ is hydrogen, the desired diastereomer produced may be (2R,3R)-(3-hydroxyphenyl)-2-pentanal. For the compound of Formula (II) where R is benzyl and $R^1$ is hydrogen, the desired diastereomer produced may be (2R,3R)-(3-benzyloxyphenyl)-2-pentanal.

(b) Step B of the 2-Step Process

Step B comprises a reductive alkylation reaction and, optionally, a deprotection of the benzyl oxygen. This step of the process comprises contacting the compound of Formula (II) with a secondary amine having Formula (V) to form the compound of Formula (III).

In embodiments in which R is hydrogen, Step B of the process comprises contacting a compound of Formula (II) with a secondary amine comprising Formula (V) in the presence of a reducing agent to form the compound of Formula (III). Generally, reductive alkylation requires an amine agent and a reducing agent.

In embodiments in which R is other than hydrogen, Step B of the process comprises contacting a compound of Formula (II) with a secondary amine comprising Formula (V) in the presence of a reducing agent to affect reductive alkylation and deprotection of the phenol to form the compound of Formula (III). Catalytic hydrogenation may be useful in this reaction.

(i) Secondary Amine of Formula (V)

The secondary amine comprising Formula (V) is a compound of formula $NR^{10}R^{11}$, wherein $R^{10}$ and $R^{11}$ are as defined above, namely, they are independently chosen from hydrocarbyl and substituted hydrocarbyl, $R^{10}$ and $R^{11}$ together may form a ring or ring system selected from carbocyclic, heterocyclic, aryl, heteroaryl, or combinations thereof. For example, $R^{10}$ and $R^{11}$ may be alkyl, substituted alkyl, aryl, or substituted aryl. In some embodiments, $R^{10}$ and $R^{11}$ together may form a ring or ring system selected from the group consisting of carbocyclic, heterocyclic, aryl, heteroaryl, and combinations thereof. Examples of suitable secondary amines include aliphatic secondary amines, aromatic secondary amines, and aliphatic-aromatic secondary amines. Non-limiting examples of suitable secondary amines include ethyl methyl amine, dimethyl amine, diethyl amine, dicyclohexyl amine, methyl cyclohexyl amine, ethyl phenyl amine, dibenzyl amine, methyl benzyl amine, ethyl benzyl amine, cyclohexyl phenyl amine, dibutyl amine, and ditertiarybutyl amine. In some embodiments, $R^{10}$ and $R^{11}$ may together form a ring, for example forming pyrrolidine or piperidine. In an exemplary embodiment, the secondary amine may be dimethylamine.

In general, the molar ratio of the compound of Formula (II) to the secondary amine comprising Formula (V) may range from about 1:1 to about 1:20. In various embodiments, the molar ratio of the compound of Formula (II) to the secondary amine comprising Formula (V) may range from about 1:1 to about 1:5, from about 1:5 to about 1:10, from about 1:10 to about 1:15, or from about 1:15 to about 1:20.

(ii) Reducing Agents

Step B may be conducted in the presence of a reducing agent. When R is hydrogen, a variety of reducing agents can be used such as hydrides, transition metals, or a transition metal catalyst in the presence of molecular hydrogen or an alternative hydrogen source. In embodiments where R is other than hydrogen, transition metals, or a transition metal catalyst in the presence of molecular hydrogen or an alternative hydrogen source may be used.

Examples of suitable reducing agents include, but are not limited to, hydrides (e.g., hydrogen iodide, hydrogen sulfide, lithium aluminum hydride, sodium borohydride, sodium cyanoborohydride, sodium triacetoxyborohydride, silicon hydride, and the like), or combinations of a metal (e.g., tin, zinc, or iron) or a metal compound (e.g., chromium chloride, chromium acetate, and the like) with an organic or inorganic acid (e.g., formic acid, acetic acid, propionic acid, trifluoroacetic acid, p-toluenesulfonic acid, hydrochloric acid, and the like), samarium iodide, Hantzsch ester, and others.

In embodiments where R is hydrogen, the weight ratio of the compound of Formula (II) to the reducing agent may range from about 1:0.3 to about 1:5. In some embodiments, the weight ratio of the compound of Formula (II) to the reducing agent may range from about 1:0.3 to about 1:0.6, from about 1:0.6 to about 1:1, from about 1:1 to about 1:2, from about 1:2 to about 1:3, or from about 1:3 to about 1:5.

The reduction in Step B may utilize catalytic hydrogenation and may be conducted in the presence of a catalyst. Representative catalysts for use in catalytic reduction methods with hydrogen include commonly used catalysts such as, for example, platinum catalysts (e.g., platinum black, colloidal platinum, platinum oxide, platinum plate, platinum sponge, platinum wire, and the like), palladium catalysts (e.g., palladium black, palladium on barium carbonate, palladium on barium sulfate, colloidal palladium, palladium on carbon, palladium hydroxide on carbon, palladium oxide, palladium acetate, palladium sponge, and the like), nickel catalysts (e.g., nickel oxide, Raney nickel, reduced nickel, and the like), cobalt catalysts (e.g., Raney cobalt, reduced cobalt, and the like), iron catalysts (e.g., Raney iron, reduced iron, Ullmann iron, and the like), and others. Further examples of transition metal catalysis and variations thereof can be found about at Section (I)(a)(i). In some embodiments, an inert substrate may be used, such as carbon, activated charcoal, alumina, barium sulfate, calcium carbonate or polystyrene. In other embodiments, the catalyst may be finely powdered or highly porous to provide a greater surface area of contact between the catalyst and the compound of Formula (II). In exemplary embodiments, the catalyst may be chosen from palladium, platinum, nickel, cobalt, and iron. In one exemplary embodiment, the catalyst may be palladium on carbon.

In various embodiments, Step B of the process utilizes catalytic hydrogenation in the presence of molecular hydrogen ($H_2$). A gas comprising molecular hydrogen may be contacted with the reaction mixture by shaking, vigorous stirring, or sparging. Typically, molecular hydrogen is added to the headspace of the reaction vessel. Molecular hydrogen may be used singly or in combination with inert atmospheric gases, such as nitrogen, argon or helium. Molecular hydrogen may be used at a pressure of about 10 to about 100 psi. In some embodiments, the pressure may be about 10 to about 20 psi, about 20 to about 30 psi, about 30 to about 40 psi, about 40 to about 50 psi, about 50 to about 60 psi, about 70 to about 80 psi, about 80 to about 90 psi, or about 90 to about 100 psi. In an embodiment, the molecular hydrogen may be present at a pressure of about 50 psi. Preferably, a gas containing greater than about 90, 95, or 99.5% hydrogen by volume is used. The gas may be mixed with an inert gas, or, in some instances with air.

In various embodiments, the weight ratio of the compound of Formula (II) to the catalyst in catalytic hydrogenation may range from about 1:0.001 to 1:1.0. In various embodiments, the weight ratio of the compound of Formula (II) to the catalyst may range from about 1:0.001 to about 1:0.005, from about 1:0.005 to about 1:0.01, from about 1:0.01 to about 1:0.05, from about 1:0.05 to about 1:0.1, from about 1:0.1 to 1:0.5 or from about 1:0.5 to about 1:1.0.

Using an alternative hydrogen source may be suitable to convert the compound of Formula (II) to the compound of Formula (III). Other suitable alternative hydrogen sources include diimide, formic acid, salts of formic acid, formic acid in the presence of an organic base, and silicon hydride. Such reactions are described in the art. In one embodiment, the hydrogen source is a diimide. Conditions for a diimide reaction may be as described in Minnaard et al., "Reduction of Carbon-Carbon Double Bonds Using Organocatalytically Generated Diimide," J. Org. Chem., 2008, 73, 9482-9485, which is hereby incorporated by reference. In various embodiments, the alternative hydrogen source may be a mixture of two of these alternative hydrogen sources, such as formate salt, and formic acid in the presence of an organic base.

In embodiments where R is hydrogen, the weight ratio of the compound of Formula (II) to the catalyst using an alternative hydrogen source may range from about 1:0.001 to 1:1.0. In various embodiments, the weight ratio of the compound of Formula (II) to the catalyst may range from about 1:0.001 to about 1:0.005, from about 1:0.005 to about 1:0.01, from about 1:0.01 to about 1:0.05, from about 1:0.05 to about 1:0.1, from about 1:0.1 to 1:0.5, or from about 1:0.5 to about 1:1.0. In embodiments where R is other than hydrogen, the weight ratio of the compound of Formula (II) to the catalyst using an alternative hydrogen source may range from about 1:0.001 to 1:1.0. In various embodiments, the weight ratio of the compound of Formula (II) to the catalyst may range from about 1:0.001 to about 1:0.005, from about 1:0.005 to about 1:0.01, from about 1:0.01 to about 1:0.05, from about 1:0.05 to about 1:0.1, from about 1:0.1 to 1:0.5 or from about 1:0.5 to about 1:1.0. In one embodiment where R is other than hydrogen, the weight ratio of the compound of Formula (II) to the catalyst may be about 1:1.

Generally, the molar ratio of the alternative hydrogen source to the compound of Formula (II) will vary depending on the alternative hydrogen source, catalyst, reaction solvent, and conditions of the reaction. The molar ratio of the alternative hydrogen source to the compound of Formula (II) may range from about 1:1 to 20:1. In various embodiments, the molar ratio of the alternative hydrogen source may range from 1:1 to about 3:1, from about 3:1 to about 6:1, from about 6:1 to about 10:1, from about 10:1 to about 15:1, or from about 15:1 to about 20:1. In an exemplary embodiment where R is other than hydrogen, the molar ratio of two alternative hydrogen sources to compound of Formula (II) may be about 1:7.5 each.

A number of reagents and conditions for reductive amination are known in the art and may be suitable for the transformation from the compound of Formula (II) to the compound of Formula (III). Examples from the literature of additional suitable reagents and conditions for reductive alkylation include Maschmeyer et al., "The Reductive Amination of Aldehydes and Ketones and the Hydrogenation of Nitriles: Mechanistic Aspects of Selectivity and Control," Adv. Synth. Catal. 2002, 334, No. 10; Tiwari et al., "Recent Development on Catalytic Reductive Amination and Applications," 1 Current Organic Chem. 12, 1093-1115 (2008); Apodaca et al., "Direct Reductive Amination of Aldehydes and Ketones Using Phenylsilane: Catalysis by Dibutyltin Dichloride." Organic Lett., 2001, Vol. 3, No. 11, 1745-1448; and Willis et al., "A One-Pot Process for the Enantioselective Synthesis of Amines via Reductive Amination under Transfer Hydrogenation Conditions," 2003, Vol. 5, No. 22, 4227-4230; each of which are incorporated by reference.

(iii) Solvent

Step B may be conducted in the presence of a solvent chosen from a polar protic solvent, a polar aprotic solvent, a non-polar solvent, and combinations thereof. Suitable solvents are described above in Section (I)(a)(vii).

The volume to weight ratio of the solvent to the compound of Formula (II) may range from about 1:1 to about 100:1. In various embodiments, the volume to weight ratio of the solvent to the compound of Formula (II) may range from about 1:1 to about 5:1, from about 5:1 to about 25:1, from about 25:1 to about 75:1, or from about 75:1 to about 100:1. In one embodiment where R is other than hydrogen, volume to weight ratio of the solvent to the compound of Formula (II) may be about 5:1.

(iv) Reaction Conditions

Step B may be conducted at a temperature that ranges from about 0° C. to about 80° C. In certain embodiments, the temperature of the reaction may range from about 0° C. to about 20° C., from about 20° C. to about 30° C., from about 30° C. to about 40° C., from about 40° C. to about 60° C., or from about 60° C. to about 80° C. In one embodiment where R is other than hydrogen, the temperature may be about 40° C. Step B may also be conducted under inert atmosphere, for example under nitrogen, argon or helium.

The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to 18 hours, or from 18 hours to 24 hours. The amount of the compound of Formula (II) remaining in the reaction mixture at the end of the reaction may be less than about 10%, less than about 5%, or less than 2%.

The compound of Formula (III) may have a yield of at least about 25%. In some embodiments the compound of Formula (III) has a yield of at least about 25%, at least about 40%, at least about 50%, at least about 60%, at least about 70%, at least about 75%, at least about 80%, at least about 85%, at least about 90%, at least about 95%, or at least about 99%.

The compound of Formula (III) may have a percent of diastereomeric excess (DE %) greater than 20%, at least about 30%, at least about 40%, at least about 50%, at least about 60%, at least about 70%, at least about 80%, at least about 90%, at least about 95%, at least about 99%, or at least about 99.5%. For the compound of Formula (II) where R is hydrogen, the desired diastereomer produced is 3-[(1R,2R)-3-(dimethyamino)-1-ethyl-2-methylpropyl] phenol.

(c) Preferred Embodiments

In exemplary embodiments, R may be hydrogen; each of $R^3$, $R^4$, $R^5$, and $R^7$ may be hydrogen; $R^1$ may be hydrogen; $R^2$ may be ethyl; and both $R^{10}$ and $R^{11}$ may be methyl. The compound of Formula (I) may be 3-hydroxyphenylboronic acid, 3-hydroxyphenyl trifluoroborate, 3-hydroxyphenylboronic acid pinacol ester, 3-hydroxyphenylboronic ester, or is derived from 3-hydroxyphenylboroxine. In Step A, the transition metal catalyst may be $[RhCl(C_2H_4)_2]_2$, the chiral ligand may be (1S,4S)-2,5-diphenylbicyclo[2.2.2]octa-2,5-diene, the amine may be 4-methylmorpholine.

In a particular embodiment, the process disclosed herein may be used to produce a compound of Formula (II), as depicted below:

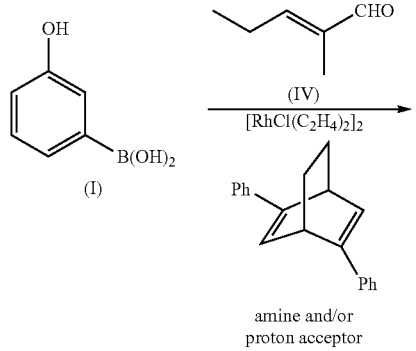

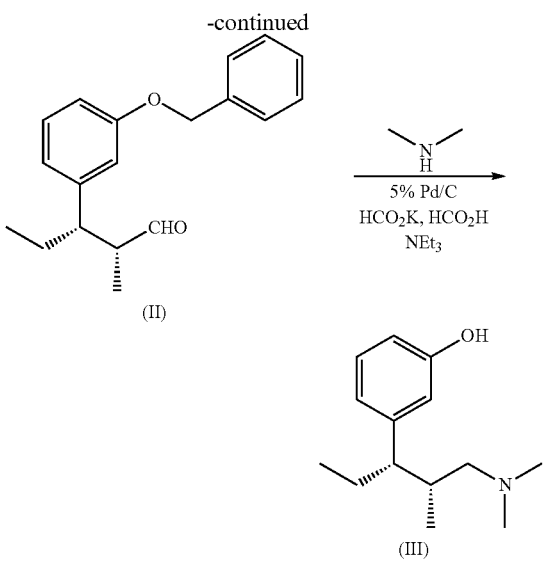

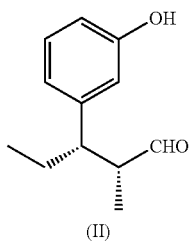

In another embodiment, R may be benzyl; each of $R^3$, $R^4$, $R^5$, and $R^7$ may be hydrogen; $R^1$ may be hydrogen; $R^2$ may be ethyl; and both $R^{10}$ and $R^{11}$ may be methyl. The compound of Formula (I) may be 3-benzyloxyphenylboronic acid, 3-benzyloxyphenyl trifluoroborate, 3-benzyloxyphenylboronic acid pinacol ester, 3-benzyloxyphenylboronic ester, is derived from 3-benzyloxyphenylboroxine. In Step A, the transition metal catalyst may be $[RhCl(C_2H_4)_2]_2$, the chiral ligand may be (1S,4S)-2,5-diphenylbicyclo[2.2.2]octa-2,5-diene, the amine may be 4-methylmorpholine or triethylamine. In Step B, the secondary amine is dimethylamine and the reduction used 5% Pd/C and a mixture of potassium formate and formic acid in the presence of triethylamine.

In a particular embodiment, the process disclosed herein may be used to produce a compound of Formula (III), as depicted below:

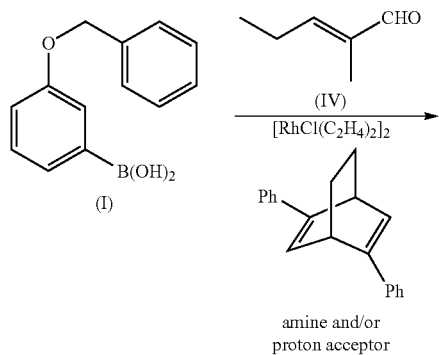

In one embodiment, Steps A and B proceed directly from one another in the order shown above. "Proceed directly," as used herein, means that intermediate reactions that add to or alter the chemical structure of the shown transformation are not used. For example, in one embodiment, Step B proceeds directly from Step A without any further steps that change the structure of the compound produced by Step A. A skilled artisan understands that chemical workups and the like may be used between steps without parting from the meaning of "proceed directly."

(II) Processes for the Preparation of a Compound of Formula (IIa)

In still another embodiment, the disclosure provides a process for preparing a compound of (IIa). The process comprises contacting a compound of Formula (Ia) with a compound of Formula (IVa) in the presence of a transition metal catalyst and a chiral ligand according to the following reaction scheme:

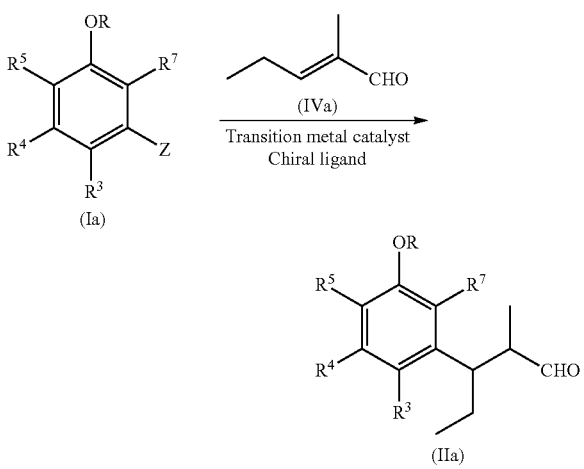

wherein:
Z is a boron containing moiety;
R is hydrogen, alkenyl, substituted alkenyl, aryl, or substituted aryl;
$R^3$, $R^4$, $R^5$, and $R^7$ are independently chosen from hydrogen, $OR^{20}$, $NR^{20}R^{21}$, $SR^{20}R^{21}$, halo, hydrocarbyl, and substituted hydrocarbyl; and $R^{20}$ and $R^{21}$ are independently chosen from hydrogen, hydrocarbyl, and substituted hydrocarbyl.

In one preferred embodiment, $R^3$, $R^4$, $R^5$, and $R^7$ are hydrogen. In another preferred embodiment, R is hydrogen or benzyl. The amount of the compound of Formula (Ia) and the compound of Formula (IVa) may be as described in Section (I).

The transition metal catalyst may be selected from those detailed in Section (I)(a)(iii). In one embodiment, the catalyst may be a rhodium (I) catalyst. In still another embodiment, the catalyst may be $[RhCl(C_2H_4)_2]_2$.

The chiral ligand may be chosen from those listed in Section (I)(a)(iv). In some embodiments, the ligand may be a diene ligand. In certain embodiments, the ligand may be 2,5-diphenylbicyclo[2,2,2]octa-2,5-diene. The 2,5-diphenylbicyclo[2,2,2]octa-2,5-diene may be chosen from (1S, 4S), (1R,4S), (1S,4R) and (1R,4R).

The reaction may be also conducted in the presence of an amine. Suitable amines may be chosen from those described in Section (I)(a)(v).

The reaction may be also conducted in the presence of a proton acceptor. Suitable proton acceptors may be chosen from those described in Section (I)(a)(vi).

The reaction is generally conducted in the presence of a solvent. Suitable solvents may be chosen from those described in Section (I)(a)(vii). The reaction conditions may be as described in Section (I)(a)(viii).

The compound of Formula (IIa) may have a yield of at least about 25%. In various embodiments, the compound of Formula (IIa) may have a yield of at least about 25%, at least about 35%, at least about 50%, at least about 60%, at least about 65%, at least about 70%, at least about 75%, at least about 80%, at least about 85%, at least about 90%, at least about 95%, or at least about 99%. The compound of Formula (IIa) may be produced with a diastereomeric excess above 20% for a given diastereomeric configuration.

Definitions

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting a particular moiety, wherein the protecting group may be removed, subsequent to the reaction for which the protection is employed, without disturbing the remainder of the molecule. Where the moiety is an oxygen atom (and hence, forming a protected hydroxy), exemplary protecting groups include ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. When the moiety is a nitrogen atom (and hence, forming a protecting amine) exemplary protecting groups include benzyl, p-methoxyphenyl (PMP), 3,4-dimethoxybenxyl (PMB)), n-silyl groups, esters (e.g., benzoate (Bz), carbonyl (e.g. p-methoxybenzyl carbonyl (Moz), tert-butyloxycarbonyl (BOC), 9-fluorenylmethyloxycarbonyl (FMOC)), acetyl, carbamates, n-silyl groups and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro and thio.

When introducing elements of the present disclosure or the exemplary embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the disclosure in detail, it will be apparent that modifications and variations are possible without departing from the scope of the disclosure defined in the appended claims.

EXAMPLES

The following examples are included to demonstrate embodiments of the disclosure. It should be appreciated by those of skill in the art that the techniques disclosed in the examples represent techniques discovered by the inventors to function well in the practice of the disclosure. Those of skill in the art should, however, in light of the present disclosure, appreciate that many changes may be made in the specific embodiments that are disclosed and still obtain a like or similar result without departing from the spirit and scope of the disclosure; therefore all matter set forth is to be interpreted as illustrative and not in a limiting sense.

The following examples exemplify the two-step process.

Example 1: Preparation of (2R, 3R)-(3-Hydroxyphenyl)-2-methylpentanal

Trans-2-methyl-2-pentenal and 3-hydroxyphenylboronic acid were reacted in the presence of a proton acceptor and amine via catalytic asymmetric 1,4-addition reaction.

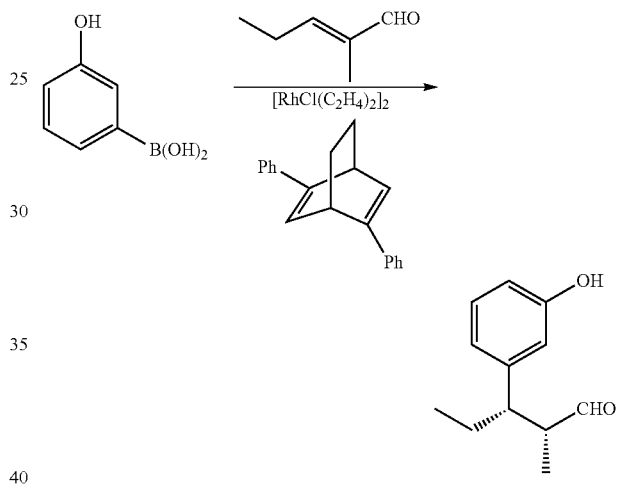

3-Hydroxyphenylboronic acid (3.64 g, 26.3 mmol) was charged to a flask and stirred under nitrogen. Degassed methanol (8.00 mL) was added and the mixture was stirred under nitrogen to completely dissolve the solids. Into a second flask was added di-µ-chlorotetraethylene dirhodium (I) (13.1 mg, 0.0336 mmol), (1S,4S)-2,5-diphenylbicyclo[2,2,2]octa-2,5-diene, (19.1 mg, 0.0739 mmol) and D-sorbitol (4.80 g, 26.3) were charged and stirred under nitrogen. Degassed methanol (6.00 mL) and trans-2-methyl-2-pentenal (3.50 mL, 30.66 mmol) were added and the mixture was stirred under nitrogen for sixty minutes. Degassed distilled water (8.00 mL) was added and the mixture was warmed from 20.8° C. to 40° C. with stirring under nitrogen over 28 minutes. 4-Methylmorpholine (0.600 mL, 5.45 mmol) was then added followed by the 3-hydroxyphenylboronic acid solution. The solution was stirred at 40° C. for eight hours. Analytical analysis revealed that the reaction contained 6.7% of the undesired isomer and 65% of the desired product.

Example 2: Preparation of 3-[(1R, 2R)-3-(dimethyamino)-1-ethyl-2-methylpropyl] phenol (Tapentadol Base)

(2R,3R)-(3-Hydroxyphenyl)-2-methylpentenal and dimethyl amine may be reacted under conditions of reductive alkylation.

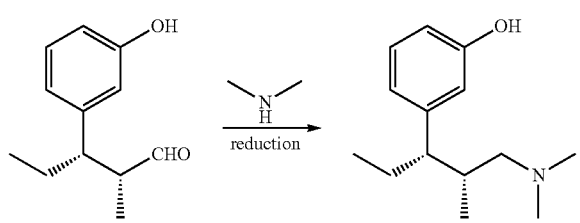

Example 2a: Preparation of 3-[(1R, 2R)-3-(dimethyamino)-1-ethyl-2-methylpropyl]phenol. (Tapentadol Base)

Into a dried reaction flask purged with nitrogen may be charged with palladium acetate (23.9 mg, 0.106 mmol), potassium formate (11.17 g, 133 mmol), dimethylamine HCl (8.66 g, 106 mmol), and triethylamine (18.5 mL, 132 mmol). The reaction flask may be cooled to 5° C. Then, a solution of the aldehyde (19.2 g, 100 mmol) in methanol (100 mL) may be added via an addition funnel. After the addition, the reaction may be warmed to 40° C. and stirred for 6 h where the reaction would be deemed complete by HPLC. The solution may be cooled to room temperature, filtered, and evaporated. To the residue, toluene (100 mL) may be added and may be stirred vigorously. 25% Aqueous sodium hydroxide may be added to adjust the pH=10.0. Stirring may be stopped and the organic layer may be allowed to separate. The organic layer may be separated and then dried over anhydrous $Na_2SO_4$. Filtration and evaporation under reduced pressure may yield tapentadol (19.9 g, 90% yield) as an oil.

Example 2b: Preparation of 3-[(1R, 2R)-3-(dimethyamino)-1-ethyl-2-methylpropyl]phenol (Tapentadol Base)

Into a Parr bottle, the aldehyde (19.03 g, 100 mmol), dimethylamine HCl (8.66 g, 106 mmol), triethylamine (18.5 mL, 132 mmol) and methanol (230 mL) may be introduced. The solution may be deoxygenated using vacuum, back filling with nitrogen (five times) then 5% Pd/C, 50% wet (92 mg) may be added. The Parr bottle may be further deoxygenated three additional times with vacuum and nitrogen then hydrogen gas (40 psi) may be introduced. The reaction may be warmed to 40° C. and stirred for approximately 6 h. After cooling the reaction to room temperature and venting the Parr bottle with nitrogen, the reaction mixture may be filtered to remove the catalyst through a fritted funnel. The funnel may then be rinsed with methanol (20 mL). To the filtrate, toluene (50 mL) and 25% aqueous sodium hydroxide may be to raise the pH to 10.0. The mixture may be stirred vigorously, and then may be allowed the settle. The organic layer may be separated, dried over anhydrous $Na_2SO_4$, filtered, and then may be evaporated under reduced pressure to yield tapentadol (19.9 g, 90% yield) as an oil.

Example 2c: Preparation of 3-[(1R, 2R)-3-(dimethyamino)-1-ethyl-2-methylpropyl]phenol (Tapentadol Base)

Into a dried reaction flask purged with nitrogen, the aldehyde (13.0 g, 67.6 mmol), dimethylamine HCl (11.0 g, 135 mmol), triethylamine (20.7 mL, 15.05 g, 14.87 mmol), and methanol (100 mL) may be introduced. The solution may be stirred for 15 minutes at room temperature then cooled to 5° C. At that time, sodium triacetoxyborohydride (31.52 g, 14.87 mmol) may be added in four portions over a 30 minute period. The reaction may be warmed to room temperature and may be stirred overnight at room temperature. Saturated sodium bicarbonate solution (100 mL) may then be slowly added to quench the reaction. After stirring for 1 hour, the quenched reaction mixture may be extracted with $CHCl_3$ (3×50 mL), the extracts may be combined, dried over anhydrous $Na_2SO_4$, filtered, and evaporated yielding tapentadol base (13.47 g, 90% yield) as an oil.

Example 3: Preparation of (2R, 3R)-3-(3-Benzyloxyphenyl)-2-methyl-pentanal

Trans-2-methyl-2-pentenal and 3-benzyloxyphenylboronic acid were reacted in the presence of a amine and/or a proton acceptor via catalytic asymmetric 1,4-addition reaction.

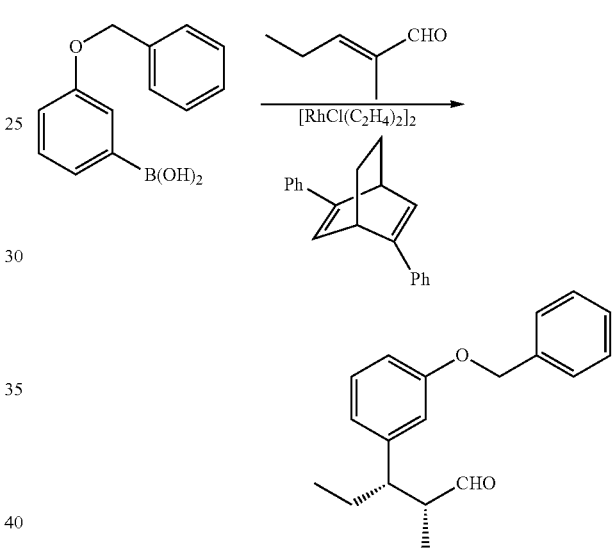

Example 3a: Preparation of (2R, 3R)-3(3-Benzyloxyphenyl)-2-methyl-pentanal

Methanol (10 mL) was degassed by heating at reflux under nitrogen then cooling to room temperature. Two vials were purged with nitrogen. 3-(Benzyloxy)phenylboronic acid (0.7504 g, 3.29 mmol) was charged to one vial. Di-μ-chlorotetraethylene dirhodium(I) (9.5 mg, 0.0244 mmol), (1S,4S)-2,5-diphenylbicyclo[2,2,2]octa-2,5-diene 14.3 mg, 0.0553 mmol), cesium carbonate (0.1500 g, 0.46 mmol), and (S)-(−)-α,α-diphenyl-2-pyrrolidinemethanol, (72.2 mg, 0.28 mmol) were charged into second vial. Each vial was purged again with nitrogen. Degassed methanol (3.0 mL) was added to the 3-(benzyloxy)phenylboronic acid and stirred under nitrogen to a clear colorless solution. Degassed methanol (5.0 mL) and trans-2-methyl-2-pentenal (0.500 mL, 4.38 mmol) were added to the vial containing the rhodium catalyst. The catalyst mixture was stirred at room temperature under nitrogen for ten minutes, and then stirred in an ice-bath for ten minutes. The 3-(benzyloxy)phenylboronic acid solution was slowly added drop wise with stirring under nitrogen over fifteen minutes to the cooled catalyst solution. Following addition, the mixture was stirred in an ice-bath for another ten minutes, and then warmed to room temperature.

After two hours, a sample of the reaction mixture was collected. Analytical analysis of the reaction mixture indicated 23% of the undesired isomer and 57.41% of the desired product.

Example 3b: Preparation of (2R, 3R)-3-(3-Benzyloxyphenyl)-2-methyl-pentanal

Methanol (50 mL) was degassed by heating at reflux under nitrogen then cooling to room temperature. 1.71% Aqueous potassium hydroxide (20 g) was degassed by heating at reflux under nitrogen then cooling to room temperature. Di-μ-chlorotetra-ethylene dirhodium(I) (26 mg, 0.067 mmol) and (1S,4S)-2,5-diphenylbicyclo[2,2,2]octa-2,5-diene (38 mg, 0.15 mmol) were charged to a nitrogen purged flask. 3-(Benzyloxy)phenylboronic acid (6.00 g, 26.3 mmol) was added and the solids were purged under nitrogen. Degassed methanol (40.5 mL) and trans-2-methyl-2-pentenal (3.49 mL, 28.4 mmol) were added. The mixture was stirred for eleven minutes under nitrogen. 4-Methylmorpholine (0.600 mL, 5.5 mmol) was added. Degassed 1.71% aqueous potassium hydroxide (19.84 g) was added. The mixture was stirred at room temperature under nitrogen for 33 hours. Toluene (58 mL), DI water (30 mL) and saturated aqueous sodium hydroxide (10 mL) were added. The mixture was thoroughly mixed, then allowed to settle. The organic layer was separated. Analytical analysis revealed that the ratio of desired to undesired diastereomers was 83:17.

Example 3c: Preparation of (2R,3R)-3-(3-Benzyloxyphenyl)-2-methyl-pentanal

Flask 1, Catalyst. Di-μ-chlorotetraethylene dirhodium(I) (126.2 mg, 0.324 mmol) and (1S,4S)-2,5-diphenylbicyclo[2,2,2]octa-2,5-diene (190.3 mg, 0.737 mmol), were stirred under nitrogen. Flask 2: Enal. Triethylamine (1.22 mL, 8.75 mmol), trans-2-methyl-2-pentenal (6.7 mL, 58.7 mmol) and methanol (10 mL) were heated at reflux under nitrogen for 30 minutes to remove air, and then cooled to room temperature. Flask 3, Phenylboronic acid. 3-Benzyloxyphenylboronic acid (10.00 g, 43.85 mmol) and methanol (20 mL) were stirred to a solution and heated at reflux under nitrogen for 30 minutes to remove air, then cooled to room temperature. The contents of reaction flask 1 were cooled in an ice bath under a nitrogen atmosphere. The contents of flask 2 (enal) were added dropwise with stirring over five minutes into flask 1 under a nitrogen atmosphere, resulting in a red solution that was stirred in the ice bath for one hour. Then, the contents of flask 3 (phenylboronic acid) were added dropwise with stirring over 112 minutes to the mixture comprising flasks 1 and 2 under a nitrogen atmosphere. Following the addition, the entire reaction mixture was stirred at room temperature for two hours. After two hours, analysis revealed 90.4% conversion and 81.0% selectivity. The reaction mixture was quenched by the addition of a solution of calcium chloride (4.87 g) in methanol (20 mL). Toluene (50 mL) was added and the mixture was washed with distilled water (1×50 mL, then 3×20 mL). The toluene layer (82.4% selectivity) was vacuum stripped from 55.6 g to 14.2 g. Methanol (50 mL) was charged and the solution was vacuum stripped from 52.4 g to 11.2 g. Methanol (50 mL) was added (solution mass 48.2 g). The product was not isolated and used directly in the reductive alkylation reaction.

Example 4: Preparation of 3-[(1R, 2R)-3-(dimethyamino)-1-ethyl-2-methylpropyl] phenol (Tapentadol Base)

(2R,3R)-3-(3-Benzyloxyphenyl)-2-methyl-pentenal and dimethylamine was reacted with a transition metal catalyst and an alternative hydrogen source to form (2R,3R)-3-(3-hydroxyphenyl)-N,N-2-trimethylpentan-1-amine (tapentadol base).

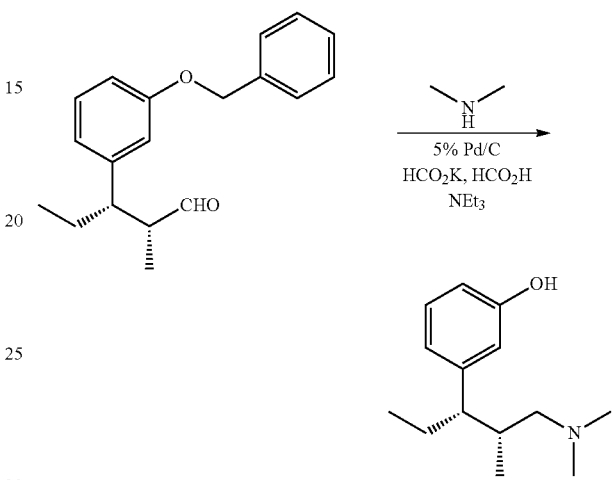

Potassium formate (14.0 g, 166.4 mmol) and dimethylamine hydrochloride (10.9 g, 133.6 mmol) were stirred in methanol (50 mL). Triethylamine (23 mL, 165 mmol) was added and the mixture was cooled in an ice-bath. 88% Formic acid (14.3 g, 273.4 mmol) was added dropwise, maintaining the temperature below 22° C. Once the addition is complete, the mixture was warmed to 20° C. 5% Palladium/carbon catalyst, 50% wet (5.00 g) was added. To this mixture was added approximately one half of the methanol solution from Example 3c (~21.92 mmol) dropwise over seven minutes. Following addition, the mixture was warmed to 40° C. then stirred for four hours. Analysis of a reaction sample indicated that the reaction was complete (no starting material remained). The mixture was filtered to remove the palladium catalyst. To the filtrate were added toluene (50 mL) and 25% aqueous sodium hydroxide to raise the pH from 7.1 to 10.0. The mixture was thoroughly stirred, and then allowed the settle. Separation of the organic layer followed by evaporation yielded tapentadol (99.0% conversion, 76.7% selectivity).

What is claimed is:

1. A process for preparing a compound of Formula (III), the process comprising:
   a) contacting a compound of Formula (I) with a compound of Formula (IV) in the presence of a transition metal catalyst and a chiral ligand to form a compound of Formula (II); and
   b) contacting the compound of Formula (II) with a secondary amine having Formula (V) to form the compound of Formula (III) according to the following reaction scheme:

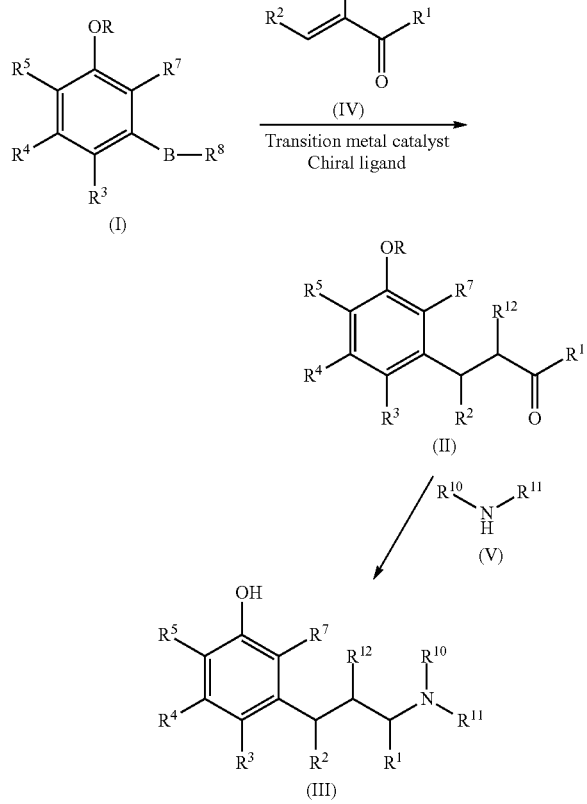

wherein:
R is hydrogen, alkenyl, substituted alkenyl, aryl, or substituted aryl;
$R^1$ is hydrogen, $OR^{20}$, $NR^{20}R^{21}$, $SR^{20}R^{21}$, hydrocarbyl, or substituted hydrocarbyl;
$R^2$ is hydrocarbyl or substituted hydrocarbyl;
$R^3$, $R^4$, $R^5$, and $R^7$ are independently hydrogen, $OR^{20}$, $NR^{20}R^{21}$, $SR^{20}R^{21}$, halo, hydrocarbyl, or substituted hydrocarbyl;
$R^8$ is

—O—$(CR^{13}R^{14})_n$—O—, —O—B—O—B—O—, or trihalo;
$R^{10}$ and $R^{11}$ are independently hydrocarbyl, substituted hydrocarbyl, or $R^{10}$ and $R^{11}$ together may form a ring or ring system selected from carbocyclic, heterocyclic, aryl, heteroaryl, or combinations thereof;
$R^{12}$ is hydrocarbyl or substituted hydrocarbyl;
$R^{13}$ and $R^{14}$ are independently hydrogen, hydrocarbyl, or substituted hydrocarbyl;
$R^{20}$ and $R^{21}$ are independently hydrogen, hydrocarbyl, or substituted hydrocarbyl; and
n is an integer of 1 or greater.

2. The process of claim 1, wherein R is hydrogen, $C_1$-$C_{10}$ alkenyl, substituted $C_1$-$C_{10}$ alkenyl, aryl, substituted aryl, or aryl($C_1$-$C_{10}$)alkyl; $R^1$ is hydrogen, alkyl, or substituted alkyl; $R^2$ and $R^{12}$ are independently alkyl or substituted alkyl; $R^3$, $R^4$, $R^5$, and $R^7$ are independently hydrogen, alkyl, substituted alkyl, hydroxyl, alkoxy, substituted alkoxy, aryl, substituted aryl, alkylaryl, or substituted alkylaryl; $R^{10}$ and $R^{11}$ are independently alkyl or substituted alkyl; and $R^{13}$ and $R^{14}$ are independently hydrogen, alkyl, aryl, alkylaryl, or organoborane.

3. The process of claim 2, wherein R is hydrogen or benzyl; $R^1$ is hydrogen; $R^2$ and $R^{12}$ are independently $C_1$-$C_{10}$ alkyl; each of $R^3$, $R^4$, $R^5$, and $R^7$ is hydrogen; and $R^{10}$ and $R^{11}$ are independently $C_1$-$C_{10}$ alkyl.

4. The process of claim 1, wherein the compound of Formula (I) is 3-hydroxyphenylboronic acid, 3-hydroxyphenyl trifluoroborate, 3-hydroxyphenylboronic acid pinacol ester, 3-hydroxyphenylboronic ester, derived from 3-hydroxyphenylboroxine, 3-benzyloxyphenylboronic acid, 3-benzyloxyphenyl trifluoroborate, 3-benzyloxyphenylboronic acid pinacol ester, 3-benzyloxyphenylboronic ester, or is derived from 3-benzyloxyphenylboroxine.

5. The process of claim 1, wherein the compound of Formula (I) and the compound of Formula (IV) are present at a molar ratio of about 1:0.5 to about 1:6.0.

6. The process of claim 1, wherein the transition metal catalyst comprises rhodium, palladium, or ruthenium; and the compound of Formula (I) and the transition metal catalyst are present at a molar ratio of about 1:0.0001 to about 1:0.1.

7. The process of claim 1, wherein the chiral ligand is a bicyclic chiral diene; and the transition metal catalyst and the chiral ligand are present at a weight ratio of about 1:0.5 to about 1:2.

8. The process of claim 1, wherein step (a) further comprises contact with a secondary or a tertiary amine; and the compound of Formula (I) and the secondary or tertiary amine are present at a molar ratio of about 1:0.01 to about 1:1.0.

9. The process of claim 8, further comprising contact with a proton acceptor; and the compound of Formula (I) and the proton acceptor are present at a molar ratio of about 1:0.001 to about 1:2.0.

10. The process of claim 1, wherein step (a) is conducted in the presence of a solvent chosen from a polar protic solvent, a polar aprotic solvent, a non-polar solvent, or a combination thereof; and the solvent and the compound of Formula (I) are present at a volume to weight ratio of about 1.0:1 to about 50:1; and step (a) is conducted at a temperature from about −10° C. to about 80° C.

11. The process of claim 10, wherein the compound of Formula (II) is obtained in a yield of at least about 25%.

12. The process of claim 1, wherein the compound of Formula (II) and the compound of Formula (V) are present at molar ratio of about 1:1 to about 1:20; step (b) is conducted in the presence of a reducing agent; and step (b) is conducted at a temperature from about −10° C. to about 80° C.

13. The process of claim 1, wherein R is hydrogen or benzyl; $R^1$ is hydrogen; $R^2$ is ethyl; each of $R^3$, $R^4$, $R^5$, and $R^7$ is hydrogen; and each of $R^{10}$, $R^{11}$, and $R^{12}$ is methyl.

14. The process of claim 13, wherein the transition metal catalyst is $[RhCl(C_2H_4)_2]_2$ and the chiral ligand is (1S,4S)-2,5-diphenylbicyclo[2,2,2]octa-2,5-diene.

15. The process of claim 14, wherein the compound of Formula (III) is 3-[(1R,2R)-3-(dimethylamino)-1-ethyl-2-methylpropyl] phenol.

16. A process for preparing a compound of Formula (IIa), the process comprising contacting a compound of Formula (Ia) with a compound of Formula (IVa) in the presence of a catalyst to give the compound of Formula (IIa):

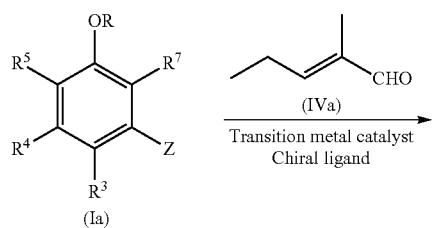

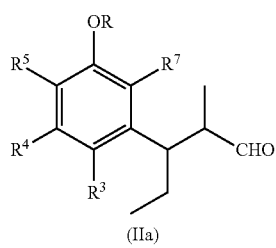

wherein:
Z is a boron containing moiety;
R is hydrogen, alkenyl, substituted alkenyl, aryl, substituted aryl, or arylalkyl;
$R^3$, $R^4$, $R^5$, and $R^7$ are independently hydrogen, $OR^{20}$, $NR^{20}R^{21}$, $SR^{20}R^{21}$, halo, hydrocarbyl, or substituted hydrocarbyl; and
$R^{20}$ and $R^{21}$ are independently hydrogen, hydrocarbyl, or substituted hydrocarbyl.

17. The process of claim 16, wherein the transition metal catalyst comprises rhodium; and the chiral ligand is a bicyclic chiral diene.

18. The process of claim 16, further comprising contact with an amine.

19. The process of claim 18, further comprising contact with a proton acceptor.

20. The process of claim 16, wherein R is hydrogen or benzyl; each of $R^3$, $R^4$, $R^5$, and $R^7$ is hydrogen, and; the transition metal catalyst is $[RhCl(C_2H_4)_2]_2$; and the chiral ligand is (1S,4S)-2,5-diphenylbicyclo[2,2,2]octa-2,5-diene.

* * * * *